(12) United States Patent
Emmons et al.

(10) Patent No.: US 7,384,457 B2
(45) Date of Patent: Jun. 10, 2008

(54) SEAL FOR GAS CHROMATOGRAPHY

(75) Inventors: William James Emmons, Hockessin, DE (US); Wesley Miles Norman, Landenberg, PA (US); Matthew S. Klee, Wilmington, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 239 days.

(21) Appl. No.: 11/255,269

(22) Filed: Oct. 21, 2005

(65) Prior Publication Data

US 2007/0089603 A1    Apr. 26, 2007

(51) Int. Cl.
*B01D 53/02* (2006.01)
(52) U.S. Cl. .................. 96/106; 95/82; 95/89; 96/101; 96/105; 73/23.41; 277/627
(58) Field of Classification Search .............. 95/82, 95/85, 86, 89; 96/101, 104, 105, 106, 107; 73/23.35, 23.39, 23.41, 23.42; 277/608, 277/627, 648, 650, 653
See application file for complete search history.

(56) References Cited

U.S. PATENT DOCUMENTS

| | | | | |
|---|---|---|---|---|
| 3,560,003 A | * | 2/1971 | Smith | 277/374 |
| 3,964,145 A | * | 6/1976 | Telang | 75/243 |
| 4,024,743 A | * | 5/1977 | Decours et al. | 72/54 |
| 4,451,365 A | * | 5/1984 | Sattler et al. | 210/198.2 |
| 4,559,063 A | * | 12/1985 | Munari et al. | 95/83 |
| 4,754,981 A | * | 7/1988 | Burns | 277/374 |
| 4,836,416 A | * | 6/1989 | Shalgi et al. | 222/48 |
| 4,954,149 A | | 9/1990 | Fullemann | |
| 5,024,884 A | * | 6/1991 | Otfinoski | 428/328 |
| 5,227,059 A | * | 7/1993 | Shepherd | 210/198.2 |
| 5,827,353 A | * | 10/1998 | O'Neil | 95/87 |
| 5,855,397 A | * | 1/1999 | Black et al. | 285/93 |
| 5,944,877 A | * | 8/1999 | O'Neil | 96/101 |
| 6,223,584 B1 | | 5/2001 | Mustacich et al. | |
| 6,442,995 B1 | * | 9/2002 | van der Maas | 73/23.35 |
| 6,662,626 B2 | * | 12/2003 | van der Maas | 73/23.35 |
| 6,719,826 B2 | * | 4/2004 | Sasano et al. | 95/87 |
| 6,742,544 B2 | | 6/2004 | Bergh et al. | |
| 6,865,926 B2 | | 3/2005 | O'Brien et al. | |
| 6,877,363 B2 | * | 4/2005 | Sattler et al. | 73/61.53 |
| 2005/0145110 A1 | * | 7/2005 | Rightnour et al. | 96/105 |

* cited by examiner

*Primary Examiner*—Duane Smith
*Assistant Examiner*—Robert A Clemente

(57) ABSTRACT

A seal forming a fluid tight connection between a gas chromatography column and a sample inlet assembly is disclosed. The seal is formed by a metal injection molding process. The seal has a first surface adapted for sealing with the sample inlet assembly and a second surface adapted for sealing with the column. The seal has an aperture extending between the first and second surfaces. A method of sealing a connection between a gas chromatography sample inlet assembly and a gas chromatography column is also disclosed. The method includes providing a seal as described above, compressing the first surface of the seal against an end of the inlet assembly, positioning the column in fluid communication with the aperture, and engaging the column with the second surface.

22 Claims, 3 Drawing Sheets

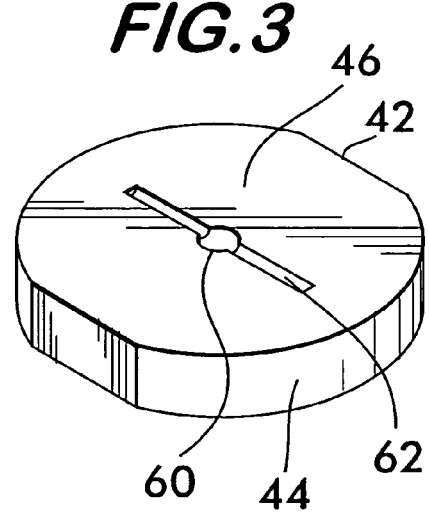
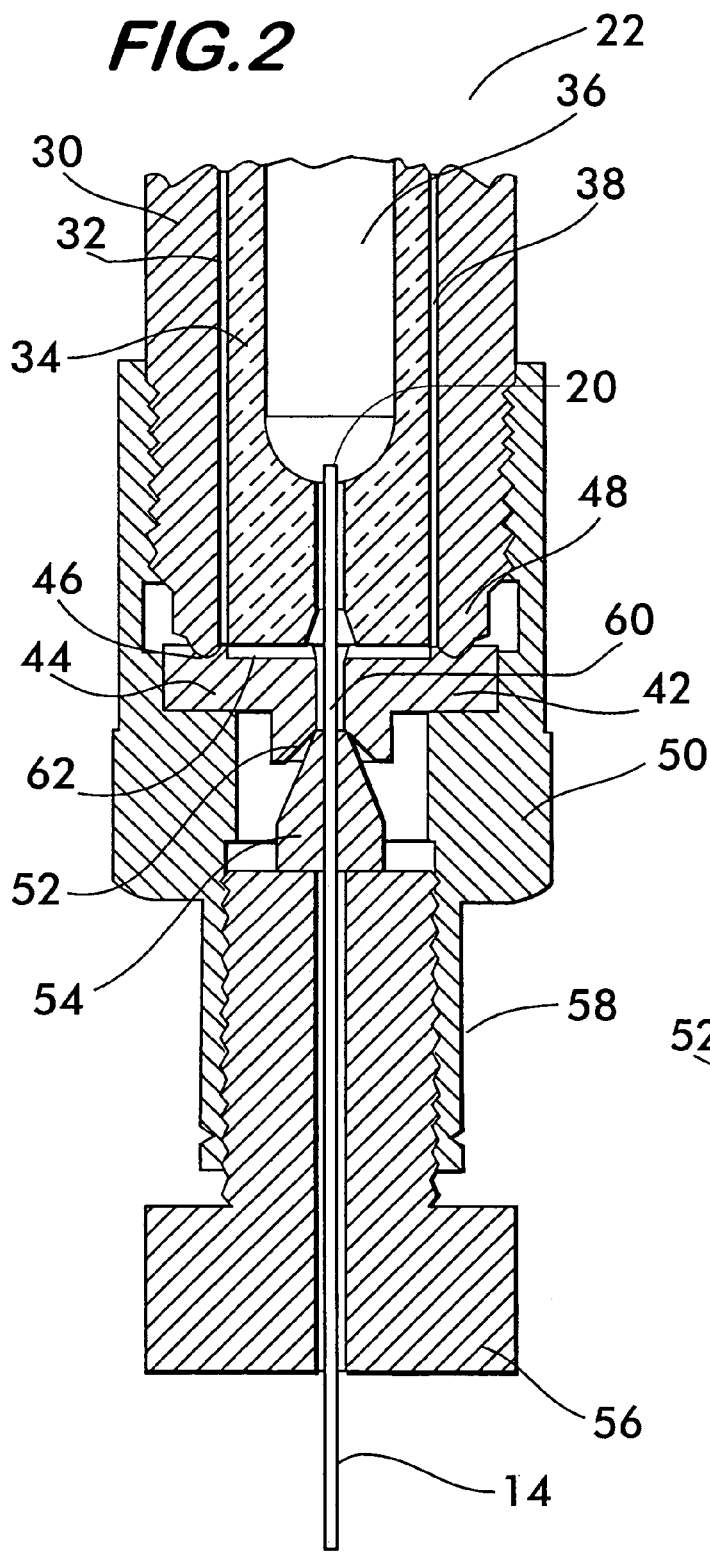
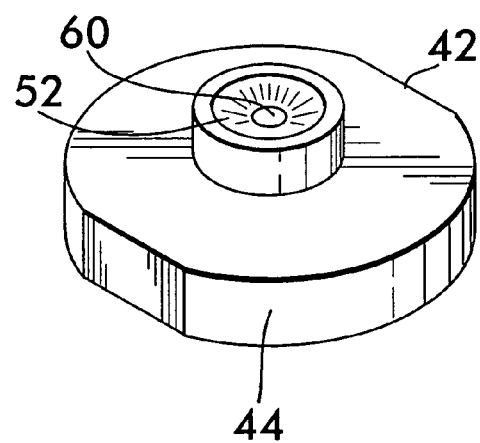

SEAL FOR GAS CHROMATOGRAPHY

BACKGROUND

Gas chromatography is a process by which one or more compounds from a chemical mixture may be separated and identified. A carrier gas, for example, an inert gas such as nitrogen or helium, flows through a tube known as a column. Large columns may have inner diameters between about 3 mm and about 8 mm and lengths between about 1 meter and about 3 meters. Capillary columns may have inner diameters between about 0.05 mm and about 1 mm and may be 100 meters or more in length. The large column may be packed with an inert packing medium coated with an active substance that interacts with compounds in the chemical mixture being analyzed. Capillary columns are preferably coated on their inner surface with the active substance.

A sample of the chemical mixture to be analyzed is injected into the column. As the sample is swept through the column with the carrier gas, the different compounds, each one having a different affinity for the active substance lining the column or coating the packing medium, move through the column at different speeds. Those compounds having greater affinity for the active substance move more slowly through the column than those having less affinity, and this speed differential results in the compounds being separated from one another as they pass through and exit the column.

The carrier gas with the separated compounds exits the column and passes through a detector, which identifies the molecules. Various types of detectors may be used, including a thermal conductivity detector, a flame ionization detector, electron capture detector, flame photometric detector, photo-ionization detector and a Hall electrolytic conductivity detector. A two dimensional plot of the detector measurements against elution time or volume, known as a chromatogram, may be made, and from the chromatogram or the digital representation thereof the compounds may be identified.

Injection of the sample chemical mixture into the column is effected using a sample inlet assembly. The sample inlet assembly has an injection port that receives a syringe for injecting the sample into the inlet assembly. The inlet assembly is connected to the column with a seal that provides a fluid tight joint between the relatively large diameter of the inlet assembly and the small diameter of the capillary column.

SUMMARY

The invention concerns a seal forming a fluid tight connection between a gas chromatography column and a sample inlet assembly. The sample inlet assembly comprises a conduit. The seal comprises a plate formed from metal powder using a metal injection molding process. The plate has a first surface on one side adapted for sealing engagement with the conduit. The plate has a second surface on an opposite side adapted for sealing engagement with the column. An aperture extends through the plate between the first and second surfaces, the aperture being positioned to provide fluid communication between the column and the sample inlet assembly.

The invention also includes a method of sealing a connection between a gas chromatography sample inlet assembly and a gas chromatography column. The inlet assembly has a conduit. The column has a ferrule. The method comprises:

providing a seal as described above made from metal powder using a metal injection molding process;
compressing the first surface of the seal against an end of the conduit;
inserting the column within the aperture; and
compressing the ferrule against the second surface.

BRIEF DESCRIPTION OF THE DRAWINGS

FIG. 2 is a view of a portion of the sample inlet assembly of FIG. 1 shown on an enlarged scale;

FIG. 3 is a perspective view of one side of a seal used with the sample inlet assembly of FIG. 2;

FIG. 4 is a perspective view of the opposite side of the seal shown in FIG. 3;

DETAILED DESCRIPTION

Figure 1:
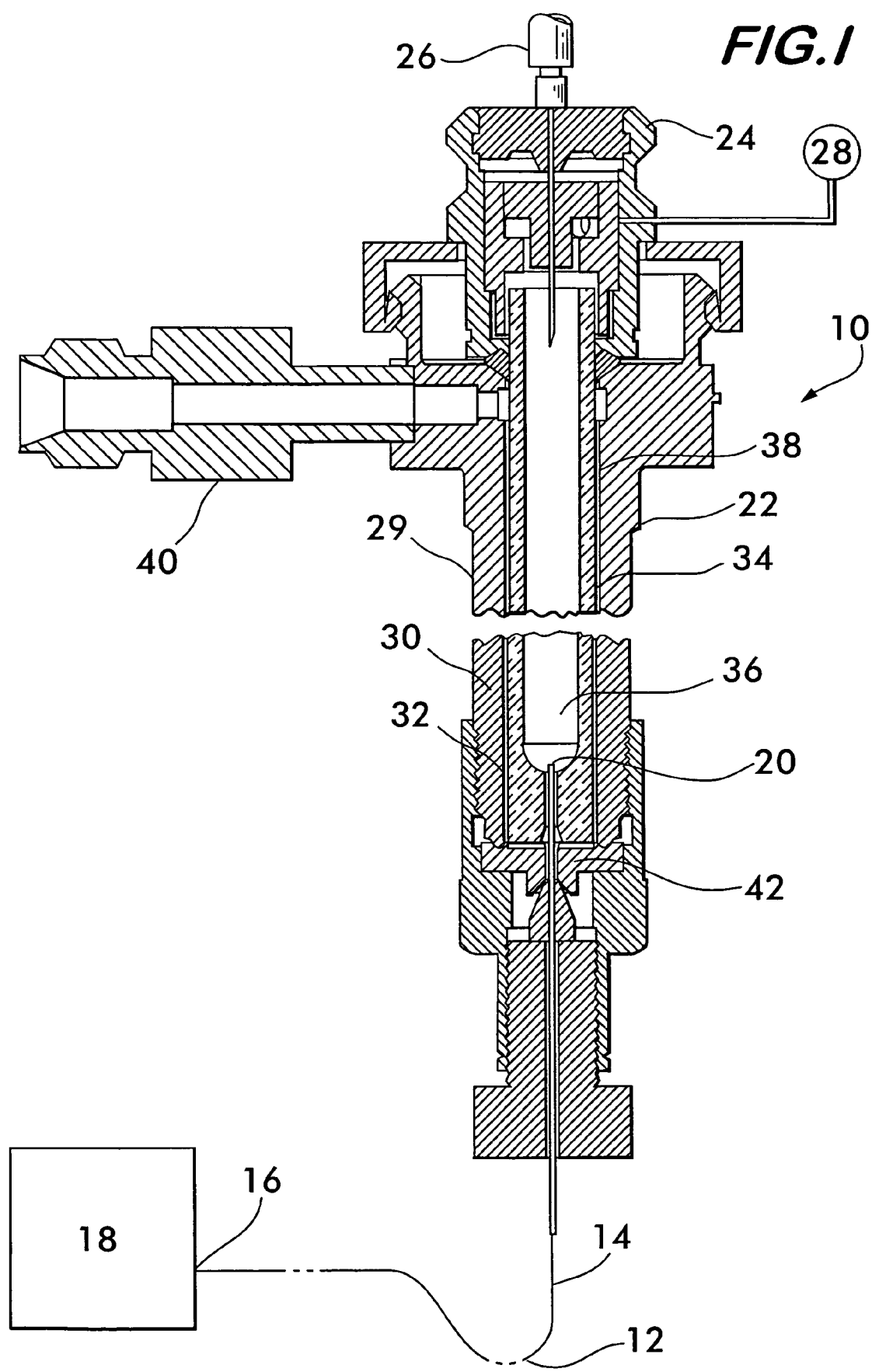
FIG. 1 is a longitudinal sectional view of a sample inlet assembly shown with a gas chromatograph.

FIG. 1 shows a gas chromatograph apparatus 10 having a column 12 comprising a capillary tube 14 lined with an active substance for separating constituent compounds from a gas mixture. Capillary tube 14 has an outlet 16 connected with a detector 18, for example, a thermal conductivity detector, a flame ionization detector, electron capture detector, flame photometric detector, photo-ionization detector, a Hall electrolytic conductivity detector or other detectors used in gas chromatography. Capillary tube 14 has an inlet 20 connected to a sample inlet assembly 22. Sample inlet assembly 22 has a sample injection port 24 which is adapted to receive a syringe 26 containing the gas sample to be analyzed. The sample inlet assembly 22 is also connected to a source of carrier gas 28, which may contain, for example, nitrogen or helium under pressure.

The sample inlet assembly 22 comprises a conduit 29 having a tubular outer shell 30, preferably made of stainless steel. Outer shell 30 has a longitudinal bore 32 in which a liner 34 is positioned. Liner 34 is preferably glass or other inert material and has a longitudinal bore 36. Preferably liner 34 has a smaller outer diameter than the inner diameter of shell 30 thereby creating an annular space 38 lengthwise between the liner and the shell. A vent port 40 is positioned within shell 30 and is in fluid communication with space 38.

As shown in FIGS. 2 and 3, a fluid tight connection of the capillary tube inlet 20 to the sample inlet assembly 22 is effected using a seal 42. Seal 42 preferably comprises a plate 44 having a first surface 46 on one side adapted for sealing engagement with an end 48 of shell 30. Plate 44 is compressed against the end of the shell preferably by a threaded nut 50 that mounts on the end of the shell and engages compatible threads thereon. It is understood that plate 44 need not be flat, but should have a shape that accommodates whatever opposing surface it is to seal against.

As shown in FIGS. 2 and 4, plate 44 has a second surface 52 on an opposite side from the first surface 46. Second surface 52 is adapted for sealing engagement with the column 12. In this example, the capillary tube 14 comprising column 12 has a ferrule 54 attached proximate to outlet 16. Second surface 52 is shaped and sized to receive the ferrule and effect a fluid tight connection when the ferrule 54 is compressed against the second surface 52. Compression of the ferrule against the second surface is effected using a threaded nut 56 that engages a nipple 58 that extends from the nut 50 used to compress plate 44 against end 48 of shell 30. An aperture 60 extends through plate 44 between the first and second surfaces. Aperture 60 receives the capillary tube 14 and allows it to pass through the plate and into the liner bore 36.

As best shown in FIG. 3, a depression 62, in this example shown as a groove, is positioned in the first surface 46 of plate 44. Depression 62 is dimensioned and positioned so that it extends between the bore 36 of liner 34 and the space 38 between the liner and the shell. The depression provides fluid communication between the liner bore 36 and the space 38. Depression 62 may have other shapes and configurations, and is not limited to the groove embodiment illustrated here.

Figure 5:
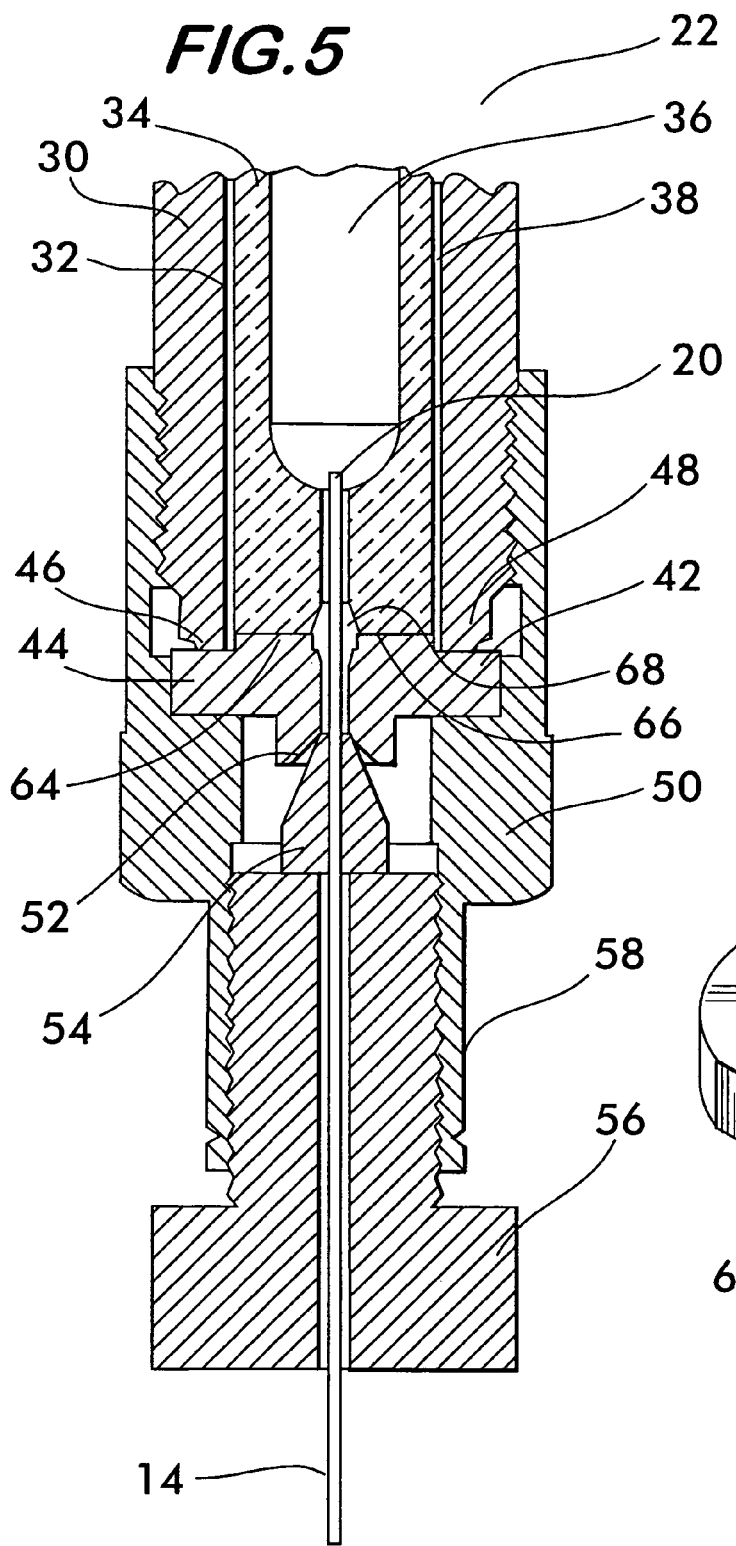
FIG. 5 is a view of a portion of an alternate embodiment of the sample inlet assembly shown on an enlarged scale.
Figure 6:
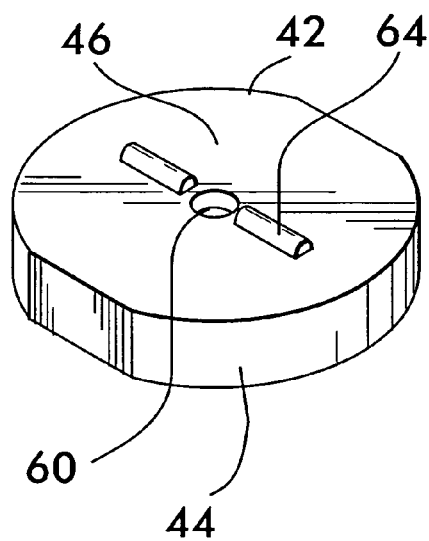
FIG. 6 is a perspective view of an alternate embodiment of a seal used with the sample inlet assembly of FIG. 5.

In an alternate embodiment, shown in FIGS. 5 and 6, a projection 64, in this example shown as a rib, is positioned on the first surface 46 of plate 44. Projection 64 extends outwardly from the first surface and engages the end 66 of liner 34 to create a gas space 68 between the liner and the plate 44 that provides fluid communication between the liner bore and the space 38 between the liner 34 and the shell 30. Although shown as a rib in the example embodiment, the projection could have other forms and shapes as well, and is not limited to a rib. The opposite side of plate 44 shown in FIG. 6 is substantially identical to that shown in FIG. 4.

Gas flow through the gas chromatograph apparatus 10 is described with reference to FIGS. 1, 2 and 5. Carrier gas flows from the source 28 and enters the sample inlet assembly 22 where it flows down the bore 36 of liner 34. The sample gas mixture to be analyzed is injected into the bore 36 through injection port 24 using syringe 26. The sample gas mixture is swept along with the carrier gas through the inlet assembly. A first portion of the sample gas mixture and the carrier gas enter the inlet 20 of the capillary tube 14 which comprises the column 12. The constituent compounds of the sample gas mixture are separated from one another as they travel through the column 12 and exit the column one after another through the outlet 16 which is connected to the detector 18 where the analysis is performed. A second portion of the gas bypasses the capillary tube inlet 20, and flows further through the liner bore 36 and along depression 62 in plate 44, best illustrated in FIG. 2. Depression 62 is in fluid communication with space 38, allowing the second gas portion to flow upwardly between the shell 30 and the liner 34 and outwardly through the vent port 40 in the shell. Alternately, the second gas portion bypasses the capillary tube inlet 20, flows further through the liner bore 36 and into the gas space 68 between the liner end 66 and the plate 44 created by the projection 64, shown in FIG. 5. Gas space 68 provides fluid communication between the liner bore 36 and the space 38 between the liner and the shell, allowing the second gas portion to flow upwardly through the space 38 and exit at the vent port 40.

Plate 44 may range in size between about 0.1 and about 0.6 inches in diameter and is made using metal injection molding. In this process, micron sized particles of metal are mixed with a thermoplastic binder. The mixture is heated to a molten state and injected into a mold. Upon curing, the molded part is subjected to a debinding process whereby the thermoplastic binder is removed. Debinding may be effected by heating, use of chemical solvents or a capillary process. After debinding, the part comprises predominantly micron sized metal particles which are then sintered at temperatures above 2400 degrees F. to drive off any remaining binder and create metallurgical bonds joining the particles together.

Unlike a machined surface, the surface formed by metal injection molding comprises a surface having randomly oriented irregularities which are not conducive to forming paths permitting leakage. This makes the metal injected molded part advantageous for use as a seal. The part may then be polished or lapped if necessary to obtain a desired surface finish.

For sealing the sample inlet assembly a surface finish having no irregularities larger than about 0.4 microns deep is advantageous. The part may then be coated to provide an inert surface that does not react with the sample compounds being analyzed, as this may adversely affect column performance. The seal is preferably made of stainless steel which may be coated with nickel, nickel alloys as well as stainless steel alloys to improve the inert quality of the surface. The nickel also acts as a bed for receiving other metal coatings, such as gold or tantalum, which further increase the chemical inertness of the part by filling surface voids and thereby reducing the surface area. Metal coating may be by vacuum deposition, sputter, or electroplating techniques. Non-metal coatings such as silica, for example in the form of silicon dioxide, may also be used to coat the seal.

The use of metal injection molding to make seals for sample inlet columns may provide one or more or other various advantages over machined parts. For example, expensive and time-consuming machining steps may be eliminated from the manufacturing process. Machined parts must also be heat treated to the annealed condition so that the part will readily deform and create a fluid tight seal when compressed against the end of the shell. This heat treating procedure can be avoided in embodiments of the present invention since metal injection molded parts emerge from the sintering process in the annealed state. It is advantageous that the seals have a hardness between about 60 and about 80 on the Rockwell B scale so that they are deformable to achieve a fluid tight seal.

What is claimed is:

1. A seal forming a fluid tight connection between a gas chromatography column and a sample inlet assembly, said sample inlet assembly comprising a conduit, said seal comprising:

a sintered metal powder plate in an annealed state and having a surface finish with randomly oriented irregularities for conforming with a mating surface, said plate having a first surface on one side engageable with said conduit, said plate having a second surface on an opposite side engageable with said column; and an aperture extending through said plate between said first and second surfaces, said aperture positioned to provide fluid communication between said column and said sample inlet assembly.

2. A seal according to claim 1, wherein said aperture is sized to receive said column.

3. A seal according to claim 1, wherein said column includes a ferrule attached thereto, said second surface having a shape adapted for sealing engagement with said ferrule.

4. A seal according to claim 1, wherein said metal powder comprises stainless steel.

5. A seal according to claim 1, wherein said plate is coated with a material selected from the group consisting of silica, nickel, nickel alloy, stainless steel alloy, gold and tantalum.

6. A seal according to claim 1, wherein said first surface has a surface finish having no irregularities larger than 0.4 microns deep.

7. A seal according to claim 1, wherein said first surface has a hardness between 60 and 80 on the Rockwell B scale.

8. A seal according to claim 1, wherein said conduit comprises an outer shell surrounding a liner, said liner having a bore therethrough, a space being positioned between said shell and said liner, said seal further comprising a depression positioned within said first surface, said depression extending from said bore of said liner to said space between said liner and said outer shell and providing fluid communication therebetween.

9. A seal according to claim 8, wherein said depression comprises a groove.

10. A seal according to claim 1, wherein said conduit comprises an outer shell surrounding a liner, said liner having a bore therethrough, a first space being positioned between said shell and said liner, said seal further comprising a projection extending outwardly from said first surface, said projection engaging an end of said liner and defining a second space between said liner and said first surface, said second space providing fluid communication between said bore and said first space.

11. A seal according to claim 10, wherein said projection comprises a rib.

12. A gas chromatography sample inlet assembly connectable to a gas chromatography column, said inlet assembly comprising:
　a shell having a shell bore;
　a liner having a liner bore, said liner being positioned within said shell bore, a first space being positioned between said liner and said shell;
　an injector port in fluid communication with said liner bore;
　a vent port in fluid communication with said first space between said liner and said shell;
　a sintered metal powder plate in an annealed state and having a surface finish with randomly oriented irregularities for conforming with a mating surface, said plate having a first surface on one side engageable with an end of said shell, said plate having a second surface on an opposite side engageable with an end of said column;
　a second space positioned between said liner and said plate, said second space providing fluid communication between said liner bore and said first space; and
　an aperture extending through said plate between said first and second surfaces, said aperture sized to receive said end of said column therein and provide fluid communication between said column and said liner bore.

13. An inlet assembly according to claim 12, wherein said column includes a ferrule attached thereto, said second surface having a shape adapted for sealing engagement with said ferrule.

14. An inlet assembly according to claim 12, wherein said metal powder comprises stainless steel.

15. An inlet assembly according to claim 12, wherein said plate is coated with a material selected from the group consisting of silica, nickel, nickel alloy, stainless steel alloy, gold and tantalum.

16. An inlet assembly according to claim 12, wherein said first surface has a surface finish having no irregularities larger than 0.4 microns deep.

17. An inlet assembly according to claim 12, wherein said first surface has a hardness between 60 and 80 on the Rockwell B scale.

18. An inlet assembly according to claim 12, wherein said seal comprises a depression positioned within said first surface, said depression extending from said liner bore to said first space and providing fluid communication therebetween.

19. An inlet assembly according to claim 18, wherein said depression comprises a groove.

20. An inlet assembly according to claim 12, wherein said seal comprises a projection extending outwardly from said first surface, said projection engaging an end of said liner and defining a second space between said liner and said first surface, said second space providing fluid communication between said liner bore and said first space.

21. An inlet assembly according to claim 20, wherein said projection comprises a rib.

22. A method of sealing a connection between a gas chromatography sample inlet assembly and a gas chromatography column, said inlet assembly having a conduit, said method comprising:
　providing a seal, said seal comprising a sintered metal powder plate in an annealed state and having a surface finish with randomly oriented irregularities for conforming with a mating surface, said plate having a first surface on one side engageable with an end of said conduit and a second surface on an opposite side engageable with said column, said plate having an aperture extending therethrough between said first and second surfaces providing fluid communication between said conduit and said column;
　compressing said first surface of said seal against said end of said conduit;
　positioning said column in fluid communication with said aperture; and
　engaging said column with said second surface.

\* \* \* \* \*